United States Patent [19]

Joy

[11] 3,937,068

[45] Feb. 10, 1976

[54] TRANSDUCER ARRANGEMENT FOR ULTRASONIC RAIL TESTER COUPLING CARRIAGES

[76] Inventor: Ivan L. Joy, 415 Delaware Drive, Ozawkie, Kans. 66070

[22] Filed: Feb. 25, 1974

[21] Appl. No.: 445,080

[52] U.S. Cl. ............................................. 73/67.7
[51] Int. Cl.² ......................................... G01N 29/04
[58] Field of Search ............. 73/67.7, 67.8 R, 67.8 S, 73/67.9, 67.5 R, 71.5 US

[56] References Cited
UNITED STATES PATENTS

| | | | |
|---|---|---|---|
| 2,672,753 | 3/1954 | Drake | 73/67.8 S |
| 3,028,751 | 4/1962 | Joy | 73/67.7 X |
| 3,251,220 | 5/1966 | Joy | 73/67.7 |
| 3,279,242 | 10/1966 | Megoloff | 73/67.8 S |
| 3,415,110 | 12/1968 | Cowan | 73/67.8 S |

*Primary Examiner*—Donald O. Woodiel
*Assistant Examiner*—Stephen A. Kreitman
*Attorney, Agent, or Firm*—Mann, Brown & McWilliams

[57] ABSTRACT

A transducer arrangement for ultrasonic rail tester coupling carriages comprising a first pair of flat angle signal transducers that are both connected to be senders and receivers and are directed in opposite directions lengthwise forwardly and rearwardly of the rail along the center of the rail head, a second pair of flat angle signal transducers that are both connected to be senders and receivers and are directly forwardly and rearwardly of the rail but are canted toward the rail gauge edge at an angle of 19°, and a third pair of flat angle signal transducers, one of which is a sender and the other of which is a receiver, that are canted in opposite directions toward the rail gauge edge at an angle of 80 degrees to provide a zig-zag signal path of multiple bounces across the rail head. The transducers act through transmitting wedges made of a material to be inefficient as a medium through which ultrasonic sound may be sent such that a significantly improved signal to noise ratio results.

2 Claims, 5 Drawing Figures

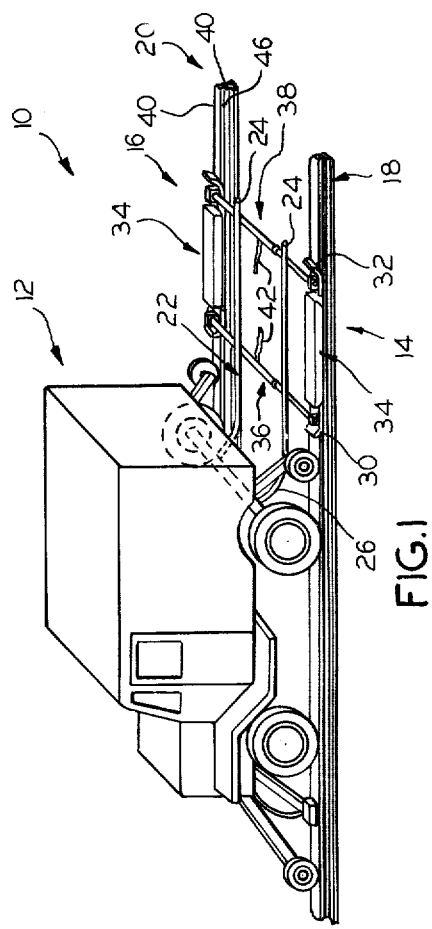
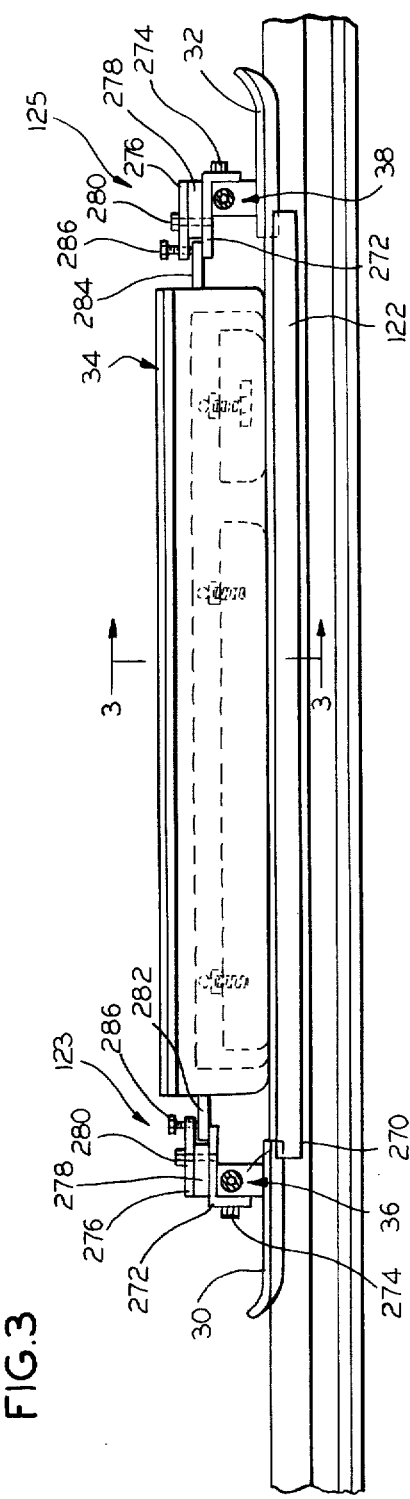
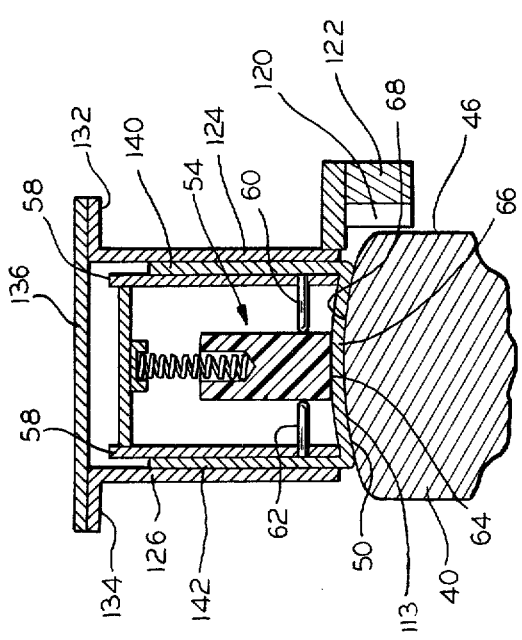

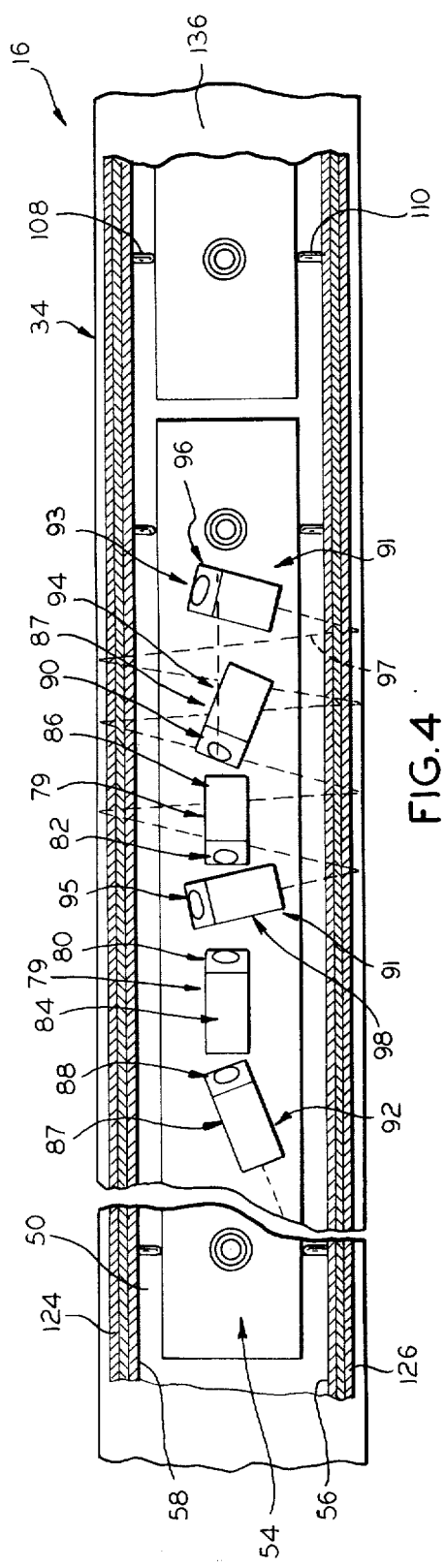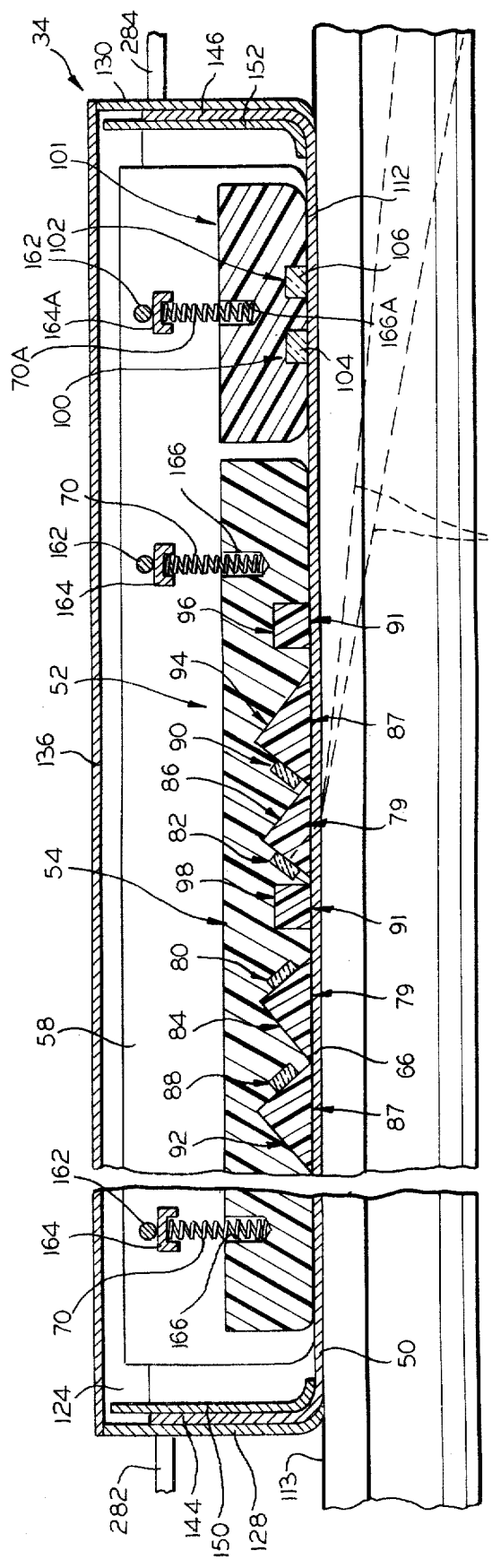

TRANSDUCER ARRANGEMENT FOR ULTRASONIC RAIL TESTER COUPLING CARRIAGES

This invention relates to a transducer arrangement for ultrasonic rail flaw tester coupling carriages, and more particularly is directed to rail flaw tester equipment of the general type shown in my U.S. Pat. No. 3,251,220, granted May 17, 1966, the disclosure of which is hereby incorporated in its entirety by this reference.

My said U.S. Pat. No. 3,251,220 discloses apparatus for progressive flaw testing of railroad track rails utilizing ultrasonics, wherein separate coupler carriages are provided for coupling to each rail, which carriages are located in trailing relation to the rail car that is equipped with the ultrasonic machines and related equipment employed. The coupling carriages each provide a coupling trough for a series of array of ultrasonic signal sending and receiving transducers that are oriented at an angle of incidence in the range 25° – 30° to inducing within the rail a shear wave travelling at a so-called "flat angle" in the range of 75° – 89°, relative to the plane of the rail head top surface, whereby the shear waves involved are oriented to be substantially normal of the flaws to be detected. Surface waves on the rail head top surface that tend to be generated by the use of such flat angles are damped by transmitting the ultrasonic signals involved through a diaphragm or a body of water on top of the rail, or through a diaphragm riding on a previously wetted rail head top surface. The ultrasonic machines involved are triggered in a predetermined cyclical sequence and the basic equipment involved is arranged to provide an integrated pictorial display of the intelligence received by the operation of the transducers.

These improvements permit practical rail flaw testing at flat angles of 80° to 85°; the nearly perpendicular path that the shear wave beams make toward the defect in the rail to be located provide a significant increase in the amount of energy reflected from the defect, and the signal has a fanning effect of approximately 15° for efficient scanning purposes.

In utilizing equipment of this type, it has been the practice to employ two transducers located at the center of the rail head and two transducers located half way between the gauge edge of the rail and the center of the rail, with the signals of the respective sending transducers being directed straight down the length of the track rail. While the flat angle pulse application of said patent sufficiently enhances ultrasonic testing efficiency to make it comparable to AAR on-rail type magnetic detector cars, difficulty has been experienced in locating small gauge edge defects lying in the lower corner of the rail head. This has been true in shelled and head checked areas and on worn curved rails.

Furthermore, ultrasonic testing has long been plagued by reflections due to conditions other than the presence of defects; these reflections, which are known as noise, are generated due to motion, grain size of the metal forming the rail, the wetting agent employed, and various relationships of moving variables in contact between the rail and the respective transducers. This problem has only been increased by attempts to build increased sensitivity into the components involved.

Another difficulty encountered utilizing electronics for rail flaw detection has been in locating a vertical split head that is located on one side of the rail head. Vertically acting transducers located at the center of the rail head can be relied on to find most vertical split heads. However, vertical splits in the head located at either side of the head may be missed, and while they are rather rare in occurrence, it is essential that they be located.

A principal object of the invention is to provide an improved transducer array arrangement for ultrasonic rail flaw tester carriages, which insures location of all small gauge edge defects lying in the lower corner of the rail head and vertical split heads which are present only on one side of the head or the other side of same, as well as the other types and kinds of defects that need to be located.

Another principal object of the invention is to operate the transducers through wedges formed from a material that is relatively inefficient as a medium through which to send sound to operate the transducer with a somewhat more narrow band width with the limiting of the band width also providing a more favorable signal to noise ratio.

Other objects of the invention are to generally improve ultrasonic coupler carriages of the type disclosed in my said patent, and to provide an ultrasonic coupling carriage arrangement that is economical of manufacture, efficient in use, and long lived in operation.

In accordance with this invention, a crystal array is provided in which the transducers employed are all of the type to provide the flat angle signal within the rail contemplated by my said patent, with the crystal array involved providing a first pair of transducers that are both connected to be senders and receivers and direct their beams in opposite directions lengthwise of the rail along the center line of the rail head forwardly and rearwardly of the rail head, a second pair of flat angle transducers that are both connected to be senders and receivers and are directed forwardly and rearwardly of the rail, but are oppositely canted toward the rail gauge edge at an angle that is preferably about 19°, and a third pair of flat angle signal transducers, one of which is a sender and the other of which is a receiver, that are canted in opposite directions toward the rail gauge edge, in signal emitting and receiving relation, at angles of 80° to provide a zig-zag signal path of three bounces across the rail head leading from the emitting transducer to the receiving transducer. All the transducers involved in the array each act through a transmitting wedge that is made of a material that is relatively inefficient as the medium for transmittal of ultrasonic sound to operate the respective transducers with a somewhat narrower band width than customary to provide a better signal to noise ratio.

Other objects, uses and advantages will be obvious or become apparent from a consideration of the following detailed description and the application drawings.

In the drawings:

FIG. 1 is a diagrammatic perspective view illustrating an ultrasonic detector car and carriage assembly for use in practicing the present invention;

FIG. 2 is a side elevational view of one of the carriages, on an enlarged scale;

FIG. 3 is a diagrammatic transverse cross-sectional view of the carriage of FIG. 2 taken substantially along line 3—3 of FIG. 2;

FIG. 4 is a diagrammatic horizontal cross-sectional view taken through the carriage of FIG. 2 in which the transducers and their associated parts are shown largely in block diagram form; and FIG. 5 is a vertical sectional view through the carriage and its crystal carrying blocks employed.

However, it is to be distinctly understood that the specific drawing illustrations provided are supplied primarily to comply with the requirements of the Patent Laws, and that the invention is susceptible of embodiments that will be obvious to those skilled in the art, and which are intended to be covered by the appended claims.

GENERAL DESCRIPTION

Reference numeral 10 of FIG. 1 generally indicates an ultrasonic progressive testing apparatus of the general type shown in my said U.S. Pat. No. 3,251,220, comprising a car 12 having operably connected thereto in trailing relation therewith carriages 14 and 16 for ultrasonically coupling to each track rail 18 and 20. The carriages 14 and 16 are secured to the car 12 through a common suspension 22 that may be constructed in accordance with my U.S. Pat. No. 3,028,751, the disclosure of which is hereby incorporated herein by this reference, In general, the suspension 22 includes support arms 24 for connection to the rear axle of the car 12 through rubber joints 26 that accommodate both vertical and lateral swinging movement of the arms 24.

Each carriage comprises fore and aft spaced rail contacting guide shoes 30 and 32 interconnected by a trough frame or box 34.

Front and rear telescoping bar units 36 and 38 are suspended in crosswise relation from the support arms 24 and are connected to the fore and aft rail contacting shoes 30 and 32 of the respective carriages to establish a reference plane relative to the heads 40 of the respective track rails 18 and 20.

Each telescoping bar unit 36 and 38 is spring biased towards an elongated relation and is fitted with a motor driven cable 42 to cause each bar unit to contract progressively during elevation of the carriages by the cables 42 and to expand progressively during lowering of the carriages to their rail engaging positions.

With the exception of carriages 14 and 16, the structure shown in FIG. 1 is illustrative of the prior art and is thus shown only diagrammetically.

The carriages are of similar construction and a description of one of the carriage 14 and 16 is applicable to the second carriage, it being understood that the carriage 14 is adapted for cooperation with the track rail 18 with reference to the gauge edge 46 of its head 40, while the other carriage 16 is adapted for cooperation with the other track rail 20 with reference to the gauge edge 46 of the latter track rail.

The showing of FIGS. 2 - 5 is concerned with the carriage 16 shown at the upper side of FIG. 1, and it will be seen that its box 34 mounts a diaphragm 50 (see FIGS. 3 and 5) on which is disposed the novel crystal array 52 of this invention shown incorporated in a fiberglass block 54 that extends lengthwise of the carriage and rests on the diaphragm 50 between a pair of runners 56 and 58 which maintain the diaphragm in conforming relation to the rail head for good ultrasonic contact, and which carry suitable guide posts 60 and 62 that operatively engage the sides of the block 54 to keep it located in a central position as the carriage slides along. As indicated in FIG. 3, the underside 64 of the block 54 is shaped to complement the shape that the underportion 66 of the diaphragm takes in conforming to the top surface 68 of the rail head 40. Block 54 is biased against the diaphragm 50, and thus against the rail head, by suitable means represented by compression springs 70 shown in the drawings.

In accordance with the present invention, the crystal array 52 generally comprises a first pair 79 of transducers in the form of crystals 80 and 82, that are respectively operatively associated with their respective wedges 84 and 86 which are located at the center of block 54 (which is intended to be approximately centered on the rail head 40) and are connected to act both as senders and receivers such that when the crystals are triggered the resulting signals are sent longitudinally of the rail in substantial parallelism with its longitudinal axis.

Block 54 also includes a second pair of transducers 87 in the form of the respective crystals 88 and 90 that are operably associated with the respective wedges 92 and 94, and are each connected both as senders and receivers and disposed to direct their signals in a canted direction relative to the longitudinal axis of the rail that is at an angle in the range of from 12 to 22°, and preferably about 19 degrees, with respect to the longitudinal axis of the rail. The transducers 87 are thus oppositively canted, relative to the longitudinal axis of the rail, and preferably at angle of about 19 degrees, and in the direction of the head gauge edge 46 for this purpose. As indicated in FIG. 4, the signals of the respective transducers 87 act forwardly and rearwardly, but with the canted angulation indicated, in the direction of the rail gauge edge.

Further in accordance with this invention, the transducers 79 and 87 are located within the block 54 so that the respective crystals 80, 82, 88 and 90 will be at the center of the block 54 and thus are located at the center of the rail head 40.

Block 54, further in accordance with this invention, includes a pair of transducers 91 comprising crystals 93 and 95 operably associated with the respective wedges 96 and 98, with the crystal 93 being connected to be a sender and the crystal 95 connected to be a receiver. The respective transducers 91 are oppositely angled, at 80° angles relative to the longitudinal axis of the rail, such that the signal emitted by the crystal 93 makes the zig-zag path indicated at 97, wherein the signal is initially directed to the gauge edge 46 of the rail head and bounces back and forth across the rail head for pick up by the crystal 95. Positioning the transducers to provide for four bounces off rail gauge edge 40, as indicated in FIG. 4, is preferred for best results. Transducers 91 are positioned so that the sender crystal 93 applies its signal at the center of the block and said signal enters the center of the block for pick up by crystal 95. Thus transducers 91 act at the center of the rail head as well as transducers 79 and 87.

All the transducers 79, 87 and 91 are arranged for the flat angle ultrasonic signal generation that is disclosed in my said U.S. Pat. No. 3,251,220, and for this purpose, the respective crystals involved are oriented at an angle of incidence of 30° so as to provide shear waves acting at angles in the range of 80° to 85° relative to the level of the rail head surface 68, as indicated at 99 in FIG. 5 for the right hand transducer 79. The sound energy on striking the rail fans into a beam 15 degrees wide, thereby "lighting up" the rail in an efficient manner.

Operably associated with the carriage 16 is a second block 101 that is mounted within the runners 56 and 58 in the same manner as block 54 and carries vertical transducers 100 and 102, in the form of suitable crystals 104 and 106 that are both connected to be senders and receivers for directing their signals vertically of the track rail. The block 101 is centered within the runners 56 and 58 by suitable guides 108 and 110, and has its undersurface 112 contoured in the same manner as the undersurface 64 of block 54. Block 101 is biased against the rail head by suitable compression spring 70A.

The wedges of transducers 79, 87, and 91 preferably have their undersurfaces contoured in the same manner as the undersurface 112 of block 54 for improved efficiency.

The transducers 79, 87, 91, 100 and 102 are incorporated in a suitable ultrasonic circuiting arrangement of the general type disclosed in my said Patent 3,251,220 whereby as the apparatus 10 moves along the track, the rails are progressively inspected for flaws that are detected by the ultrasonic system involved.

As the apparatus 10 moves along the track, the signals provided by the transducers detect flaws within the rail. The beams provided by the transducers of crystal array 52 act at a flat angle of 80° – 85° relative to the level of the rail head surface 68, with the surface waves that would tend to be generated by such a flat angle being dampened by the diaphragm 50 and a film of water that is applied to the rail head surface 68 in advance of the respective carriages 14 and 16 by suitable equipment carried by the car 12, in accordance with said U.S. Pat. No. 3,251,220 (indicated at 113 in FIGS. 3 and 5).

It is to be noted that in the crystal array 52, all transducers are located to operate substantially at the center of the rail head, where best ultrasonic contact can be maintained. The transducers 79 effect transmission of their signals straight down the rail in the center of the rail head and down into the web as depicted by the signal path indicated for the right hand transducer 79 of FIG. 5. These two transducers are particularly efficient in locating small irregularities in the center of the rail head and more especially in all types of butt welded rail.

The transducers 87 locate all gauge edge defects, and are particularly useful in locating small defects lying in the lower corner of the rail head gauge edge, and those located in shelled and head checked territory and on worn curved rail. With the arrangement indicated for transducers 87 it is now possible to locate a gauge edge defect such as a hack saw mark 1/16th of an inch deep in the bottom corner of the rail head on the gauge side. Despite the sensitivity of operation provided by the transducers 87, these transducers do not provide objectionable pick up of the upset in all types of butt welds.

The signal provided by the right hand transducer 91 of FIG. 4 follows the zig-zag path 99 that is indicated in FIG. 4 for pick up by the left hand transducer 91 provides contact with the rail that can be constantly monitored to show the relative efficiency of the ultrasonic contact that is being made by the carriage with the rail head. These transducers 91 also locate vertical split head and large transverse defects, as will be shown by attenuation in the signal. For vertical split heads the attenuation will be by a factor of 50 percent in the normal signal.

While the vertical transducers 100 and 102 will find most split head defects which lie above the web of the rail, the transducers 91 are particularly useful in locating vertical split heads that appear on either side of the rail head which are relatively rare in occurrence.

Further, in accordance with this invention, the wedges that the crystals of transducers 79, 87 and 91 act through are formed from a material which is relatively inefficient as a medium through which to send ultrasonic sound, whereby an improvement in the sound to noise ratio is obtained on the order of 15 percent, as compared with using a material which is an efficient medium through which to send ultrasonic sound. For this purpose, the wedges 84, 86, 92 and 94 and 96 and 98 are formed from a solid ultrasonic signal transmitting medium in the form of a suitable epoxy resin, such as the products sold under the trademark Epoxylite (Nos. 205 or 4102) by Epoxylite Corporation of El Monte, California, charged with powdered glass or powdered silicon carbide (sand). The velocity of the sound signal in passing through the epoxy material is approximately one-half the velocity that the signal would have in passing through, for instance powdered glass. By charging the epoxy material with a material such as powdered silicon carbide, or powdered glass, the signal will be transmitted through the wedges in a variety of velocities, which breaks up the phase of the signal transmission, thus attenuating the transmission, and providing a desirable narrow band width. While other powdered materials will also break noise sound velocities, the powdered materials specified are preferred as they seem to result in less noise and signal attenuation.

The resulting lossy nature of the wedges employed also helps eliminate the generation of surface waves at the respective transducers. The narrow band width from the electronic standpoint provided by utilizing the lossy wedges of this invention also contributes to the improvement in the signal to noise ratio.

SPECIFIC DESCRIPTION

The shoes 30 and 32 may be of any suitable wear resisting construction, each shoe having a wear strip 120 suitably secured thereto which slides along the rail gauge edge 46 under the biasing action provided by the telescoping bar units 36 and 38, holding the respective carriages properly against the rail during movement of the same along the track. The respective wear strips 120 are connected together in tandem relation by bar 122.

The carriage box or trough 34 is suitably connected to the respective shoes at either end of same, where indicated at 123 and 125, to support same and permit lateral adjustment of the box relative to the shoes, for adjusting the box 34 as desired laterally of the rail being tested. While the weight of box 34 is supported by the shoes, the box is disposed as indicated in FIG. 3 so that the diaphragm 50 has firm engagement with the rail head. The connection of the box 34 to the shoes is diagrammatically illustrated in FIG. 2 wherein it will be seen that each shoe includes an upright member 270 (to which the respective telescoping bar units 36 and 38 are respectively connected), each having an angle member 272 adjustly (vertically) secured thereto by suitable bolts 274. The respective angle members have secured thereto a top plate 276 resting against spacer 278, which are both secured in place on the respective members 272 by bolts 280. The respective flanges 282 and 284 of the box 34 rest on the respective angle members 272 and are clamped in place by set screws 286 applied to the respective top plates 276 at the desired positioning of the box 34 laterally of the rail.

The box 34 comprises side walls 124 and 126 (see FIG. 2) suitably joined to end walls 128 and 130, with the side walls 124 and 126 being suitably flanged as at 132 and 134, respectively for application thereto of a cover plate 136 that may be secured in place in any suitable manner as by employing bolts or the like.

The diaphragm 50 is formed from any suitable plastic rubber or the like flexible material and has a trough-like form defining side walls 140 and 142 and end walls 144 and 146, which are integral with the central portion 166 of the diaphragm on which the blocks 54 and 99 rest. The diaphragm side walls 140 and 142 are closely received between the respective runners 56 and 58 so that the central portion 166 is in overlying relation with the major portion of the transverse dimension of the rail head surface 68. At the forward end of the box or frame 34, the diaphragm wall 144 is held in place by a suitable clamp plate 150 while at the rear end of the box the diaphragm wall is held in place by suitable clamp plate 152, with the clamp plates 150 and 152 being suitably secured to the respective end walls 128 and 130 of the box or frame 34.

The runners 56 and 58 are vertically disposed in the spaced apart relation indicated in FIGS. 3 and 4 and are maintained in spaced apart relation by suitable cross rods 162 that interconnect the same as well as the action of the guide arms 60 and 62 and 108 and 110, which are carried by the respective runners 56 and 58, and engage the side walls of the respective blocks 54 and 101. The runners 56 and 58 hold this central portion 166 of the diaphragm against the rail head surface 68 while permitting it to flex and distort as necessary to conform to changes in the rail surface contour. The guide posts or arms 60, 62, 108 and 110 maintain the position of the respective blocks 54 and 101 against displacement laterally of the runners 56 and 58, but the fit is loose enough to permit these blocks to move vertically in following the contour of the rail head.

In the form shown, the compression springs 70 act between suitable spring seats 164 and suitably fixed to the respective cross rods 162, and recesses 166 formed in the block 54. Similarly, the compression spring 70A acts between suitable spring seat 164A and recess 166A formed in the block 101.

The crystals employed as part of the transducers described may be of the general type described in my said U.S. Pat. No. 3,251,220.

The crystals and wedges of the respective transducers are suitably embedded in the block 54 to mount them in operating position in accordance with the principles herein stated. Similar remarks apply to the transducers of block 101, these being conventional vertical crystals.

Water is preferably applied to each rail adjacent the front of the vehicle 12 to allow sufficient time for the rail head to become wetted, and also just in advance of each box 34, between the box and the forward shoe 30, for best results.

The foregoing description and the drawings are given merely to explain and illustrate the invention and the invention is not to be limited thereto, except insofar as the appended claims are so limited, since those skilled in the art who have the disclosure before them will be able to make mofidications and variations therein without departing from the scope of the invention.

I claim:

1. In an ultrasonic apparatus for progressive railroad track rail flaw testing for detecting flaws in railroad track rails including a multi-element ultrasonic signal pulse emitting and echo receiving assembly riding on the rail head in its operative position and comprising a plurality of separate ultrasonic transducer devices mounted in a carriage adapted to be coupled to the rail head in the operative position of the assembly by means for damping out surface waves on the rail head, through which means the ultrasonic signals are to act, the improvement wherein:

said transducer devices comprise:
    a pair of transducer devices,
        one of said pair of transducer devices being positioned to emit ultrasonic test signal pulses canted at an angle of approximately 80° with respect to the centerline of the rail and in the direction of the rail gauge edge, in the operative position of the assembly,
    said devices of said pair of devices being spaced longitudinally of the rail in the operative position of the assembly for permitting the signal pulses of said one device of said pair of devices to make a zig-zag path across the rail head
    said pair of transducer devices being located in the assembly to be disposed, in the operative position of the assembly, at the center of, and on top of, the top surface of the rail head and to act at an angle of incidence relative to the rail head top surface to produce in the rail as a result of their signal impulses ultrasonic waves travelling at flat angles on the order of 80° to 85° relative to the level of the rail head top surface.

2. The improvement set forth in claim 1 wherein:
    said spacing of said devices of said pair of devices permits four bounces of the signal thereof off the rail gauge edge in the operative position of the assembly.

* * * * *